United States Patent [19]

Schmalzl et al.

[11] Patent Number: 4,873,228
[45] Date of Patent: Oct. 10, 1989

[54] 2-OXO-4-CARBOXY-PYRIMIDINES AND THEIR USE AS ANTI-MALARIA AND ANTI-CANCER AGENTS

[75] Inventors: Karl J. Schmalzl, Victoria; Suresh C. Sharma, Prospect; Richard I. Christopherson, Paddington, all of Australia

[73] Assignees: The University of Melbourne, Melbourne; The University of Sydney, Sydney, both of Australia

[21] Appl. No.: 91,761

[22] Filed: Sep. 1, 1987

[30] Foreign Application Priority Data

Sep. 2, 1986 [AU] Australia ................ PH7811
Sep. 22, 1986 [AU] Australia ................ PH8161

[51] Int. Cl.$^4$ ............... A61K 31/505; C07D 401/06; C08B 37/00
[52] U.S. Cl. ........................ 514/49; 514/274; 536/22; 544/310; 544/311; 544/312; 544/315; 544/316; 544/318
[58] Field of Search ........ 544/310, 311, 312, 315, 544/316, 318; 514/274, 49; 536/22

[56] References Cited

U.S. PATENT DOCUMENTS 4,684,655 8/1987 Atwal .................. 544/316

OTHER PUBLICATIONS

Klein et al., Chem Abstracts, vol. 73, No. 9, 45768e (1970).

Primary Examiner—Mary C. Lee
Assistant Examiner—J. Richter
Attorney, Agent, or Firm—Ladas & Parry

[57] ABSTRACT

A compound for use as an inhibitor for the enzyme dihydroorotase and which is of general formula (I)

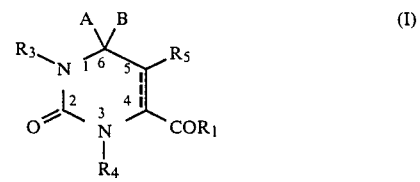

where either
(i) A and B together are =S
or
(ii) A is —H, and B is —$COR_2$ or —$SR_6$; and
$R_1$ and $R_2$ which may be the same or different are —OH; alkyloxymethyl, a di-, tri- or polypeptide group, —OR where R is saturated or unsaturated $C_{1-16}$ alkyl, $C_{1-16}$ alkyloxymethyl, or 4-alkyl-piperidinyl-alkyl, —NR'R' where each R' is independently selected from —H, saturated or unsaturated $C_{1-16}$ alkyl, or any group above to be hydrolyzed in vivo to hydroxy;
$R_3$ and $R_4$ which may be the same or different are —H, $C_{1-6}$ alkyl, hydroxy $C_{1-16}$ alkyl, hydroxy $C_{1-6}$ ether group, tetrahydrofuranyl, tetrahydropyranyl, a sugar or acetylated sugar group, hexylcarbamyl, methylglycine-N-carbonyl, or any group able to be hydrolysed in vivo to —H;
$R_5$ is —H, halo, or $C_{1-6}$ alkyl;
$R_6$ is $C_{1-6}$ alkyl or 1-methyl-4-nitroimidazol-5-yl; and the dotted line represents a double bond which may be absent or present in the 4-5 position. The compounds are useful as anti-cancer and anti-malarial drugs.

22 Claims, No Drawings

2-OXO-4-CARBOXY-PYRIMIDINES AND THEIR USE AS ANTI-MALARIA AND ANTI-CANCER AGENTS

This invention relates to novel compounds, their preparation and compositions thereof. In a particular aspect this invention relates to inhibitors for the enzyme dihydroorotase, and compounds for their preparation.

The biosynthesis of pyrimidine nucleotides is essential for the production of genetic material (DNA and RNA) in all living cells. In mammalian cells, pyrimidine nucleotides (UTP and CTP) can be synthesized from simple precursors via a de novo pathway or from preformed nucleosides (uridine and cytidine) present in blood using a salvage pathway. The malarial parasite (*Plasmodium falciparum*) lacks the salvage pathway for utilisation of pyrimidine nucleosides and can only synthesize UTP and CTP via the de novo route.

Several useful anti-cancer drugs have been developed which inhibit particular enzymes catalysing biochemical reactions late in the pathway leading to the synthesis of DNA. Methotrexate is a tight-binding inhibitor of the enzyme dihydrofolate reductase and is used with other drugs in the cure of childhood leukaemia. 5-fluorouracil is converted to 5-fluorodeoxy UMP (FdUMP) within cells and as a deoxy nucleoside monophosphate is a tight-binding inhibitor of the enzyme thymidylate synthetase, 5-fluorouracil is used to treat certain solid tumours in humans. Both of these drugs have a selective toxicity for cancer cells because many types of cancer grow more rapidly than normal cells of the body and must therefore synthesize DNA and RNA at a faster rate. In addition, cancer cells spend more time in S-phase of the cellular growth cycle where they are susceptible to such drugs. Both methotrexate and 5-fluorouracil block the synthesis of DNA by inhibiting, directly or indirectly, thymidylate synthetase. We have been developing new inhibitors against dihydroorotase, the third enzyme of the de novo pyrimidine pathway. Earlier research by Dr. Christopherson resulted in elucidation of the catalytic mechanism of dihydroorotase. In the reaction catalysed, it is proposed that carbamyl aspartate is converted through a transition state where the 2 oxygen atoms at position 6 of the dihydropyrimidine ring interact strongly with a zinc atom bound to the surface of the enzyme. The transition state than collapses to give the product, dihydroorotate. We have synthesized sulphur and carboxy analogues of dihydroorotate which are tight-binding inhibitors of dihydroorotase.

The present invention provides a compound for use as an inhibitor for the enzyme dihydroorotase and which is of general formula (I)

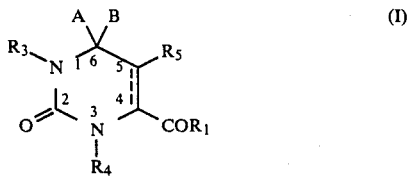

where either
(i) A and B together are =S
or
(ii) A is —H, and B is —COR$_2$ or —SR$_6$; and R$_1$ and R$_2$ which may be the same or different are —OH; a di-, tri- or polypeptide group, —OR where R is saturated or unsaturated C$_{1-16}$ alkyl, C$_{1-16}$ alkanoyloxymethyl, or 4-alkyl-piperidinylalkyl; —NR'R' where each R' is independently selected from —H, saturated or unsaturated C$_{1-16}$ alkyl, or any group able to be hydrolysed in vivo to hydroxy;

R$_3$ and R$_4$ which may be the same or different are —H, C$_{1-6}$ alkyl, hydroxy C$_{1-16}$ alkyl, hydroxy C$_{1-6}$ ether group, tetrahydrofuranyl, tetrahydropyranyl, a sugar or acetylated sugar group, hexylcarbamyl, methylglycine-N-carbonyl, or any group able to be hydrolysed in vivo to —H;

R$_5$ is —H, halo, or C$_{1-6}$ alkyl;

R$_6$ is C$_{1-6}$ alkyl or 1-methyl-4-nitroimidazol-5-yl; and the dotted line represents a double bond which may be absent or present in the 4-5 position.

One preferred group of inhibitors which is believed to act by binding tightly to the zinc-enzyme is formed when A and B together are =S and R$_1$ is OH. Another preferred group which is believed to act by binding tightly as an analogue of the transition state of the reaction is formed when A is H, B is —COR$_2$, R$_1$ and R$_2$ are OH.

When R$_1$ or R$_2$ are alkyl, they are preferably methyl. The di-, tri- or polypeptide group may be formed with any of the naturally occuring amino acids, such as alanyl-glutamate, glutamyl-alanine, and glycyl-glycine. The —OR group is preferably acetoxymethoxy or 4-methylpiperidinylethoxy.

When R$_3$ or R$_4$ is a sugar or acetylated sugar they may be pentose or hexose sugars. The group able to be hydrolysed in vivo may be, for example, hydroxyethoxy-methyl. R$_6$ is preferably methyl.

Particularly preferred compounds include:
Hexahydro-2-oxo-6-thioxo-4-pyrimidinecarboxylic acid (referred to as TDHO);
2-oxo-1,2,3,6-tetrahydropyrimidine-4,6-dicarboxylic acid (referred to as HDDP); and
(4R*, 6R*)-2-oxo-hexahydro-4,6-pyrimidine dicarboxylic acid (referred to as HTDP).

The invention also comprises prodrugs i.e. compounds which are converted in vivo to a compound of formula (I), particularly esters or salts. Preferred esters are non-polar so as to be lipid soluble and able to be enzymically hydrolysed in vivo to the free acid.

The invention also provides pharmaceutical compositions which comprise a compound of formula (I) together with a pharmaceutically acceptable carrier. The composition may be in a form suitable for injection, oral or rectal administration, or a slow-release formulation.

The compounds are useful as anti-cancer and anti-malarial drugs.

For the treatment of cancer, it may be advantageous to concurrently administer an agent which also blocks the alternative salvage pathway mentioned above, preferably by including it in the same formulation as the inhibitor. Such blocking agents include dipyridamole, dilazep and nitrobenzyl thioinosine.

In the treatment of malaria, it may be useful to coadminister the inhibitor with the pyrimidine nucleotide precursors uridine or cytidine, preferably in the same formulation.

Compounds of formula (I) can exhibit keto-enol tautomerism. Accordingly, the fact that a structure is drawn to represent one tautomer or that nomenclature suggests one tautomer is not to be considered as restrictive. When in the enol form the hydroxyl group may be readily substituted.

The present invention also provides a method for the production of a compound of general formula (I) which comprises
(A) when A and B together are =S; thiating a compound of formula (II)

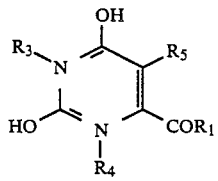
(II)

wherein R₁, R₃, R₄ and R₅ are as above, followed by reduction of at least one double bond;
(B) when A is H, and b is —COR₂; oxidising a compound of formula (III)

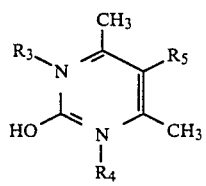
(III)

wherein R₃, R₄ and R₅ are as above, followed by reduction of at least one double bond.

When A is H and B is COR₂ the method comprises oxidising the methyl groups of a corresponding pyrimidine compound to carboxyl groups and partially reducing the pyrimidine ring to dihydropyrimidine preferably using a metal dissolved in a protic solvent. Catalytic hydrogenation over a metal catalyst may achieve further reduction. It is generally preferred to carry out reduction on the ester rather than the acid itself.

Various techniques are known for reducing ring double bonds in compounds where A and B are =S and of them we prefer those utilizing a protonating solvent or those using an inert solvent containing a proton source with a metal or metal alloy or other reducing agent. Preferred is to react an ester, or other derivative of 6-thioorotic acid or tautomer thereof in dry acetic acid with zinc, to produce the zinc salt. Thereafter, the free acid, ester, or other derivative may be obtained.

6-thioorotic acid is known per se and a procedure for making it has been published. However, we have also devised new syntheses which comprise the thiation of orotic acid or a derivative of L-dihydroorotic acid. Preferred reagents include phosphorus pentasulphide and 2,4-bis(4-methoxyphenyl)-1,3,2,4-dithia diphosphetane-2,4-disulphide, (the latter being commonly known as Lawesson's Reagent). Preferably the thiating conditions for orotic acid itself comprise heating in pyridine with phosphorus pentasulphide at 60°-100° C., more preferably about 80° C., for half to two hours. Excess heat and/or excess reaction time may lead to further reaction or decomposition.

The following Examples illustrate the present invention.

EXAMPLE 1 (Thioorotic acid)

(2-hydroxy-6-mercapto-4-pyrimidinecarboxylic acid or 1,2,3,6-tetrahydro-2-oxo-6-thioxo-pyrimidine-4-carboxylic acid). Anhydrous orotic acid (2,6-dihydroxy-pyrimidine-4-carboxylic acid) (50 mg) was dissolved in warm pyridine (5 ml) and after the addition of phosphorous pentasulphide (215 mg) the stirred mixture was heated in an oil bath to 90° C. over a period of 30 minutes. Stirring and heating at 90° C. were continued for a further 30 minutes. After cooling, the pyridine solution was decanted from the undissolved residue at the bottom of the reaction vessel and concentrated in a rotary evaporator under water pump vacuum at 40° C., the resultant residue was stirred with 10% hydrochloric acid (3 ml) for 15 minutes at room temperature and the precipitated product was filtered, washed with a small amount of water and ethanol and dried to yield an apricot orange crystalline solid (35 mg) consisting of a mixture of unreacted orotic acid and the desired title compound.

EXAMPLE 2 (thiodihydroorotic acid, TDHO)

(2-oxo-6-thioxo-hexahydro-pyrimidine-4-carboxylic acid). 6-Thioorotic acid (350 mg) was suspended in dry, redistilled glacial acetic acid (200 ml) which had been bubbled with nitrogen. The mixture was stirred at room temperature for 30 minutes and stirred and heated in an oil bath at 55°-60° C. for 30 minutes by which time the orange solid had dissolved completely. Excess zinc powder (500 mg) was added in portions over 10 minutes to the vigorously stirred solution at 60° C. while nitrogen was bubbled through.

The temperature of the oil bath was maintained at 60°-64° C. with vigorous stirring of the sealed flask for a further 50 minutes during which time the colour of the solution had turned dark red. The solution was then cooled to room temperature. (If it is desired to isolate TDHO as the zinc salt at this stage of the preparation the solution is filtered rapidly through a sintered glass funnel with suction, the filtrate is frozen in a liquid nitrogen bath, and lyophilised under vacuum at room temperature).

To prepare the free acid, anhydrous oxalic acid (831 mg) in dry redistilled glacial acetic acid (20 ml) was then added to the reaction mixture. After swirling and agitation for 20 minutes at room temperature, the precipitated zinc oxalate and any unreacted zinc powder were removed by suction through a sintered glass funnel, the filtrate was frozen in a liquid nitrogen bath, and then lyophilised at room temperature at a vacuum of 0.05 to 0.1 mm Hg. Finally the resulting light brown solid was heated in an oil bath at 60° C. for 5 hours under 0.05 mm Hg vacuum to remove any remaining volatile organic acids. The product (332 mg) contained approximately 65% by weight TDHO (yield 71%) and approximately 8% by weight dihydroorotic acid (DHO).

EXAMPLE 3

Methyl L-2,6-dioxo-hexahydropyrimidine-4-carboxylate

L-2,6-Dioxo-hexahydropyrimidine-4-carboxylic acid (L-dihydroorotic acid) (1.13 g, 7.15 mmol) was suspended in dry methanol (100 ml). Dry hydrochloric acid gas was bubbled into the mixture for 15 min. The reaction mixture was refluxed for 1.5 h, cooled and the solvent removed to give a white solid. The crude product was recrystallized from acetone to give methyl L-2,6-dioxo-hexahydropyrimidine-4-carboxylate as colourless needles (920 mg, 75%), m.p. 183°–185°. ¹H n.m.r. (DMSO/CDCl₃): δ10.15, br s, NH; 7.80, br s, NH; 4.20, ddd, $J_{4,5}$ 7.2 Hz, $J_{4,5}$ 3.6 Hz, $J_{4,NH}$ 3.6 Hz, H4; 3.73, s, $CO_2CH_3$; 2.86, dd, $J_{5,5}$ 16.8 Hz, $J_{5,4}$ 7.2 Hz, H5; 2.69, dd, $J_{5,5}$ 16.8 Hz, $J_{5,4}$ 3.6 Hz, H5. $^{13}C$ n.m.r. (DMSO/CDCl$_3$): δ169.4, 166.9, 151.7, 51.1, 47.8, 31.4. $\nu_{max}$ (KBr) 3256, 3092, 1734, 1700, 1474, 1437, 1375, 1345, 1291, 1240, 1216, 1194, 1028, 850 cm$^{-1}$.

EXAMPLE 4

Methyl L-2-oxo-6-thioxo-hexahydropyrimidine-4-carboxylate

Methyl L-2,6-dioxo-hexahydropyrimidine-4-carboxylate (50 mg. 0.29 mmol) was dissolved in anhydrous tetrahydrofuran (5 ml) with stirring at room temperature. Lawesson's reagent (71 mg. 0.17 mmol) was added and the reaction mixture stirred for 24 h. The solvent was removed and the yellow crystalline residue subjected to chromatography (flash silica, light petroleum then ether) to give the pure thione. Recrystallization from chloroform gave methyl L-2-oxo-6-thioxo-hexahydropyrimidine-4-carboxylate as pale yellow needles (46 mg. 84%), m.p. 157°–159°.

$^1H$ n.m.r. (CDCl$_3$): δ10.40, br s, NH; 8.00, br s, NH; 4.25, m, H4; 3.74, s $CO_2CH_3$; 3.27 and 3.13, m, 2×H5. (acetone): δ 4.42, m, H4; 3.75, s, $CO_2CH_3$; 3.33, m, 2×H5.

EXAMPLE 5

(2-Oxo-hexahydropyrimidine-4,6-dicarboxylic acid, HTDP)

2-Hydroxypyrimidine-4,6-dicarboxylic acid was reduced to HTDP by direct hydrogenation in the presence of a metal catalyst such as rhodium by the method of Hanze (A. R. Hanze (1967) J. Amer. Chem. Soc. 89 6720–6725).

EXAMPLE 6

2-Hydroxypyrimidine-4,6-dicarboxylic acid (HDP)

4,6-Dimethyl-2-hydroxypyrimidine (9.97 g, 0.08 mol) was dissolved in sodium hydroxide (2.5M, 100 ml) and heated to 70°. A solution of potassium permanganate (54.0 g, 0.34 mol) in water (360 ml) was heated to 70° and added dropwise over 1½–2 h to the solution. The reaction mixture was allowed to stir at 70° for 2 h, cooled and filtered. Any purple colour in the filtrate was removed with sodium metabisulphite. The filtrate was concentrated under reduced pressure and a cold solution of concentrated hydrochloric acid (10M, 35 ml) was added at 5° to pH 2–3. The reaction mixture was filtered and recrystallized from water to yield 2-hydroxypyrimidine-4,6-dicarboxylic acid (6.56 g, 44%), as colourless crystals, m.p.>250° (dec.).

$^1H$ n.m.r. spectrum (D$_2$O): δ 6.31, s, H5.

Mass spectrum m/z: 96 (M$^+$-2×$CO_2$, 8%), 68 (5), 44 (100).

EXAMPLE 7

Dimethyl 2-hydroxypyrimidine-4,6-dicarboxylate

2-Hydroxypyrimidine-4,6-dicarboxylic acid (6.66 g. 36.2 mmol) was refluxed with acetyl chloride (5.68 g. 72.4 mmol) in anhydrous methanol (350 ml) for 2 h. The reaction mixture was cooled and the solvent removed to give a pale yellow solid. The crude product was recrystallized from methanol to give colourless needles of dimethyl 2-hydroxypyrimidine-4,6-dicarboxylate (3.75 g. 62%), m.p. 186°–188°. $^1H$ n.m.r. spectrum (DMSO/CDCl$_3$):

δ 7.84, s, H5; 3.99, s, 2×$CO_2CH_3$ $\nu_{max}$ (KBr) 3460, 3433, 3329, 1747, 1672, 1653, 1611, 1457, 1442, 1267, 1234, 1159, 1103, 1044, 885, 763 cm$^{-1}$.

Mass Spectrum m/z: 212 (M$^+$, 8%), 182 (24), 154 (100), 139 (11), 121 (25), 91 (31), 81 (14), 66 (20).

EXAMPLE 8

Dimethyl 2-oxo-1,2,3,6-tetrahydropyrimidine-4,6-dicarboxylate

Dimethyl 2-hydroxypyrimidine-4,6-dicarboxylate (1.0 g. 4.7 mmol) was dissolved in warm acetic acid (17M. 70 ml) and heated to 70°. Zinc dust (1.5 g. 22.9 mmol) was added to this stirred solution portionwise over a period of 1 h. Each addition of a zinc portion was accompanied by a purple colour change of the reaction mixture. This colour slowly dissipated, then further zinc was added in similar fashion until completion. The resulting mixture was stirred at 70° for 30 min. The reaction mixture was filtered and washed with acetic acid (17M, 2×10 ml). The filtrate was evaporated to dryness under reduced pressure to give a colourless oil. The residual oil was dissolved in chloroform (100 ml), filtered and the solvent removed to give colourless crystals. The crude product was recrystallized from methanol to give dimethyl 2-oxo-1,2,3,6-tetrahydropyrimidine-4,6-dicarboxylate as colourless prisms, (283 mg. 28%) m.p. 177°–179°

$^1H$ n.m.r. spectrum (DMSO/CDCl$_3$): δ 8.13, br s, NH; 7.17, br s, NH; 5.79, ddd, $J_{5,6}$ 5.3 Hz, $J_{5,NH}$ 1.7 Hz, $J_{5,NH}$ 1.7 Hz, H5; 4.74, dd, $J_{6,5}$ 5.3 Hz, $J_{6,NH}$ 2.4 Hz, H6; 3.78, s, $CO_2CH_3$.

$\nu_{max}$ (KBr) 3450, 1757, 1729, 1685, 1472, 1457, 1349, 1289, 1223, 1176, 1111, 1044, 1008, 984, 845, 741 cm$^{-1}$.

Mass Spectrum m/z: 214 (M$^+$, 5%), 213 (5), 155 (100), 123 (25), 95 (71), 68 (13).

EXAMPLE 9

(4R*, 6R*)-Dimethyl 2-oxo-hexahydropyrimidine-4,6-dicarboxylate

Dimethyl 2-hydroxypyrimidine-4,6-dicarboxylate (1.42 g. 6.7 mmol) was dissolved in methanol (300 ml) and hydrogenated over 10% Pd/C catalyst. The reaction mixture was filtered and the methanol removed under reduced pressure. The crude product was recrystalized from methanol/ether to yield (4R*, 6R*)-dimethyl 2-oxo-hexahydropyrimidine-4,6-dicarboxylate (1.27 g, 88%) as colourless needles m.p. 178°–179°.

$^1H$ n.m.r. spectrum (DMSO/D$_2$O): δ 2.28, ddd, $J_{5ax,5eq}$ 14 Hz, $J_{5ax,4ax(6ax)}$ 6 Hz, 5ax; 2.36, ddd, $J_{5eq,5ax}$ 14 Hz, $J_{5eq,4ax(6ax)}$ 4 Hz, 5eq; 4.12, dd, $J_{4ax(6ax), 5ax}$ 6 Hz, $J_{4ax(6ax),5eq}$ 4 Hz, 4ax and 6ax. $^{13}C$ n.m.r. spectrum (DMSO/D$_2$O): δ 25.1, C5; 50.3 and 51.8, 2×$CH_3$, C4 and C6; 151.5, C2; 171.5, 2×$CO_2CH_3$.

$\nu_{max}$ (KBr) 3249, 3099, 2963, 1751, 1695, 1533, 1450, 1253, 1202, 1042, 817, 776 cm$^{-1}$.

Mass Spectrum m/z: 216 (M$^+$, 10%), 157 (100), 114 (73), 97 (34), 82 (23).

EXAMPLE 10

General hydrolysis procedure

The ester (0.5 mmol) was heated under reflux in a solution of sodium hydroxide (1M, 2.5 ml) for 30 min and cooled. The reaction mixture was filtered, acidified with concentrated hydrochloric acid (10M) to pH 3–4 and the solvent was lyophilized. The mixture was recrystallized from water.

(A) (4R*, 6R*)-2-oxo-hexahydropyrimidine-4,6-dicarboxylic acid (HTDP)

Dimethyl 2-oxo-hexahydropyrimidine-4,6-dicarboxylate was hydrolyzed by the general procedure above to yield (4R*, 6R*)-2-oxo-hexahydropyrimidine-4,6-dicarboxylic acid (36%) as white crystals.

$^1$H n.m.r. spectrum (D$_2$O): δ 2.10, ddd, $J_{5ax,5eq}$ 13.5 Hz, $J_{5ax,4ax(6ax)}$ 5.0 Hz, 5eq; 4.13, dd, $J_{4ax(6ax),5ax}$ 8.0 Hz, $J_{4ax(6ax),5eq}$ 5.0 Hz, 4ax and 6ax.

Mass Spectrum m/z: 144 (M-CO$_2$, 1%), 100 (6), 71(4), 56 (5), 44 (100).

(B) 2-oxo-1,2,3,6-tetrahydropyrimidine-4,6-dicarboxylic acid (HDDP)

Dimethyl 2-oxo-1,2,3,6-tetrahydropyrimidine-4,6-dicarboxylate was hydrolysed by the general procedure above to yield 2-oxo-1,2,3,6-tetrahydropyrimidine-4,6-dicarboxylic acid (50%) as colourless needles.

$^1$H n.m.r. spectrum (D$_2$O): δ 6.08, d, $J_{5,6}$ 5.0 Hz, H5; 4.90, d, $J_{6,5}$ 5.0 Hz, H6.

Mass spectrum m/z: 158, (M-CO, 0.4%), 142 (0.1), 126 (0.1), 110 (0.4), 90 (5), 56 (15), 46 (80), 45 (100), 44 (89).

(C) 2-Oxo-1,2,3,6-tetrahydropyrimidine-4,6-dicarboxylic acid (HDDP)

2-Hydroxypyrimidine-4,6-dicarboxylic acid (239 mg. 1.30 mmol) was suspended in acetic acid (17M, 60 ml) at 70° with stirring. Zinc dust (600 mg. 9.17 mmol) was added portionwise over a period of 30 min and the mixture was stirred for 1 h at 70° then cooled to room temperature. A solution of oxalic acid (200 mg. 2.22 mmol) in acetic acid (10 ml) was added and the reaction mixture allowed to stand for 5 h. The mixture was filtered and the filtrate evaporated to dryness. The residue was dissolved in hot water (5 ml), filtered and cooled to 4° to 4 days. 2-Oxo-1,2,3,6-tetrahydropyrimidine-4,6-dicarboxylic acid was obtained as off-white crystals (58 mg, 24%).

EXAMPLE 11

General procedure for the preparation of amides from esters

The ester (1 mmol) was dissolved in methanol (20 ml) and cooled to 0°-5°. Ammonia was bubbled through the solution while the mixture was stirred for 40 min. The reaction vessel was stoppered and the mixture allowed to warm to room temperature and left to stand for 16 h. The reaction mixture was filtered and insoluble material washed with methanol to give a white solid.

(A) 2-Hydroxypyrimidine-4,6-dicarboxamide

Dimethyl 2-hydroxypyrimidine-4,6-dicarboxylate was ammonolysed by the general procedure above to yield 2-hydroxypyrimidine-4,6-dicarboxamide (93%).

$^1$H n.m.r. spectrum (D$_2$O): δ 7.51, s, H5. $^{13}$C n.m.r. spectrum (D$_2$O): δ 171.5, 171.4, 163.6, C2, C3 and C5, 2×CONH$_2$; 104.9, C5.

Mass spectrum m/z: 182 (M+, 35%), 139 (100), 93 (20), 67 (40), 44 (62).

(B) (4R*, 6R*)-2-Oxo-hexahydropyrimidine-4,6-dicarboxamide

Dimethyl 2-oxo-hexahydropyrimidine-4,6-dicarboxylate was ammonolysed by the general procedure given above to yield (4R*, 6R*)-2-oxo-hexahydropyrimidine-4,6-dicarboxamide (72%) as a white solid.

EXAMPLE 12

Preparation of Methoxy Acetate Esters

A mixture of the acid (1.0 mmol), bromomethyl acetate (1.1 mmol) and anhydrous triethylamine (1.2 mmol) in anhydrous acetonitrile (10 ml) and anhydrous acetone (10 ml) was stirred at room temperature for 48 h. The reaction mixture was filtered and the solent removed. The residue was recrystallized from acetone to give colourless crystals of triethylamine hydrobromide, filtered and the solvent removed from the filtrate.

EXAMPLE 13

Preparation of Glycylglycine Ethyl Esters

A solution of the pyrimidine carboxylic acid (3.00 mmol) IIDQ (2-isobutoxy-1-isobutoxycarbonyl-1,2-dihydroquinoline) (3.75 mmol), glycylglycine ethyl ester hydrochloride (3.75 mmol) and anhydrous triethylamine (3.75 mmol) in anhydrous dimethylformamide (25 ml) were stirred at 50°–55° for 36 h. The solvent was removed under reduced pressure, the residue dissolved in ethanol (25 ml) and poured into hydrochloric acid (1M, 200 ml). The precipitate was filtered, dried and purified by chromatography (flash silica).

This preparation was of general use in the synthesis of peptide, dipeptide and tripeptide esters.

EXAMPLE 14

Preparation of the Pyrimidine Dipeptide Acids

The pyrimidine glycylglycine ethyl ester (1.0 mmol) was dissolved in a solution of hydrochloric acid in glacial acetic acid (1M. 6 ml). The solution was stirred at room temperature for 2 h and the HCl removed under reduced pressure. Acetic acid was removed by freeze-drying and the residue was washed with anhydrous ether to give a white solid, which was further purified by HPLC.

EXAMPLE 15

Preparation of N-Hexylcarbamoyl Pyrimidines

The pyrimidine (1.0 mmol) and hexyl isocyanate (1.5 mmol) were heated in pyridine (4 ml) at 90° for 1 h, cooled to room temperature and the solvent removed at 50° under reduced pressure. The residue was dissolved in hot ethanol (5 ml), filtered and cooled to 0°–4° for 24 h to give the crystalline product.

EXAMPLE 16

Preparation of N-Methoxycarbonylmethylcarbamoyl Pyrimidines

These compounds were prepared by the general method described above using 1-methoxycarbonylmethylisocyanate.

TEST 1 (Purification of Dihydroorotase)

Dihydroorotase has been purified by an established procedure from a mutant hamster cell line which overproduces the target enzyme by more than 100-fold (P. F. Coleman, D. P. Suttle and G. R. Stark (1978) in "Methods in Enzymology" (P. A. Hoffee and M. E. Jones eds.) Vol. 51, pp 121-134, Academic Press, New York; P. F. Coleman D. P. Suttle and G. R. Stark (1977) J. Biol. Chem. 252, 6379-6385). Purified dihydroorotase was stored at -70° C. in a solution containing 30% (v/v) dimethyl sulphoxide, 5% (v/v) glycerol, 50 mM KCl, 4 mM L-glutamine, 4 mM L-aspartate, 0.1 mM EDTA and 1 mM dithiothreitol.

TEST 2 (Inhibitory Potency of TDHO)

Dihydroorotase catalyses the conversion of N-carbamyl-L-aspartate to L-dihydroorotate. To assess the effects of a potential inhibitor of this target enzyme, the rate of conversion of L-dihydroorotate to N-carbamyl-L-aspartate catalysed by dihydroorotase was measured in the presence of a range of concentrations of the inhibitor. For a tight-binding inhibitor like TDHO, extremely low concentrations are sufficient to abolish all dihydroorotase activity. To illustrate the inhibitory potency of TDHO, results of the following experiment are presented. Assay mixtures for dihydroorotase activity contained in a total volume of 25 ul, 50 mM K.Hepes buffer pH 7.4, 5% (v/v) glycerol 12.5 $\mu$M L-[$^{14}$C]dihydroorotate (specific radioactivity 47.1 Ci/mol), and TDHO concentrations ranging from 0–1.50 $\mu$M containing a 30-fold molar excess of $ZnCl_2$. Catalysis was initiated by addition of 39 ng of dihydroorotase. The rate of conversion of L-[$^{14}$C]dihydroorotate to N-[$^{14}$C]carbamyl-L-aspartate was measured in the presence of different concentrations of TDHO, using established procedures (R. I. Christopherson, T. Matsuura and M. E. Jones (1978) Analytical Biochemistry 100, 184–187). The assay mixture lacking TDHO had the fastest reaction velocity. while the lowest velocity measured was in the presence of the highest concentration of TDHO. The resultant data are plotted as the reciprocal of reaction velocity (l/v) versus the concentration of TDHO from which a value for the dissociation constant ($K_i$ value) for TDHO from the enzyme-TDHO complex can be obtained.

From the data a $K_i$ value of 53 nM was calculated indicating a very strong interaction between TDHO and the target enzyme, dihydroorotase in vitro. The results also show that $ZnCl_2$ alone (at the same concentrations) has only a moderate inhibitory effect, and the free acid of TDHO (in the absence of $Zn^{2+}$) is a less effective inhibitor with a $K_i$ value of 4.5 $\mu$M.

TEST 4 (Inhibitory Potency of HDDP)

Assay mixtures for dihydroorotase activity contained in a total volume of 25 $\mu$l:50 mM K.Hepes buffer pH 7.4, 5% (v/v) glycerol, 12.5 $\mu$M L-[$^{14}$C]dihydroorotate (specific radioactivity 47.1 Ci/mol), and HDDP concentrations ranging from 0–5 $\mu$M. Catalysis was initiated by addition of 39 ng of dihydroorotase. The rate of conversion of L-[$^{14}$C]dihydroorotate to N-[$^{14}$C]carbamyl-L-aspartate was measured in the presence of different concentrations of HDDP, in a similar manner to Test 3.

From the data a $K_i$ value of 0.48 $\mu$M was calculated indicating a strong interaction between HDDP and the target enzyme, dihydroorotase, in vitro.

We claim:
1. A compound of the formula (I)

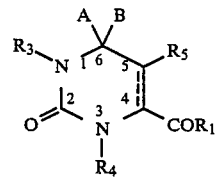

wherein either (i) A and B together are =S or (ii) A is —H, and B is $COR_2$ or —$SR_6$; and $R_1$ and $R_2$ which may be the same or different are —OH; a di-, tri- or polypeptide group, —OR where R is saturated or unsaturated $C_{1-16}$ alkyl, $C_{1-16}$ alkanoyloxymethyl, or 4-alkyl-piperidinyl-alkyl, —NR'R' where each $R_1$ is independently selected from —H or saturated or unsaturated $C_{1-16}$ alkyl, $R_3$ is H, $R_4$ is —H, $C_{1-6}$ alkyl, hydroxy $C_{1-16}$ alkyl, hydroxy $C_{1-6}$ ether group, tetrahydrofuranyl, tetrahydropyranyl, a sugar group, hexylcarbamyl, or methylglycine-N-carbonyl, $R_5$ is —H, halo, or $C_{1-6}$ alkyl; $R_6$ is $C_{1-6}$ alkyl or 1-methyl 1-4-nitroimidazol-5-yl; and the dotted line represents a double bond which may be absent or present in the 4–5 position, provided that A and B shall not be =S when R, is OH, $R_4$ is —H and $R_5$ is —H.

2. A compound according to claim 1 wherein A and B together is =S and a single bond is present in the 4–5 position.

3. A compound according to claim 1 wherein A is —H and B is —$SR_6$ and a single bond is present between $C_4$ and $C_5$.

4. A compound according to claim 1 wherein A and —H and B is —$COR_2$ and a double bond is present between $C_4$ and $C_5$.

5. A compound according to claim 1 wherein A is —H and B is —$COR_2$ and a single one is present between $C_4$ and $C_5$.

6. A compound according to claim 1 wherein $R_3$ is —H and $R_4$ is —H or ribsoyl.

7. A compound according to claim 2, wherein $R_3$ is —H and $R_4$ is —H or ribsoyl.

8. A compound according to claim 3, wherein $R_3$ is —H and $R_4$ is —H or ribsoyl.

9. A compound according to claim 4, wherein $R_3$ is —H and $R_4$ is —H or ribsoyl.

10. A compound according to claim 5, wherein $R_3$ is —H and $R_4$ is —H or ribsoyl.

11. A compound according to claim 6, wherein $R_3$ is —H and $R_4$ is —H or ribsoyl.

12. A compound which is 2-oxo-6-thioxo-hexahydropyrimidine-4-carboxylic acid.

13. A compound which is 2-oxo-1,2,3,6-tetrahydropyrimidine-4,6-dicarboxylic acid.

14. A compound according to claim 2, wherein $R_1$ is hydroxy, methoxy, acetoxymethoxy, amino or glycyl glycine, $R_3$ is —H and $R_4$ is —H or ribosyl.

15. A compound according to claim 3 wherein $R_6$ is methyl or, 1-methyl-4-nitroimidazol, $R_1$ is hydroxy, methoxy, acetoxymethoxy, amino or glycyl glycine, $R_3$ is —H and $R_4$ is —H or ribosyl.

16. A compound according to claim 4, wherein $R_1$ and $R_2$ are each hydroxy, methoxy, acetoxymethoxy, amino or glycyl glycine, $R_3$ is —H and $R_4$ is —H or ribosyl.

17. A compound according to claim 5, wherein $R_1$ and $R_2$ are each hydroxy, methoxy, acetoxymethoxy, amino or glycyl glycine, $R_3$ is —H and $R_4$ is —H or ribosyl.

18. A composition which comprises an anti-malaria effective amount, or an anti-cancer effective amount of a compound according to claim 1 together with a pharmaceutically acceptable carrier.

19. The composition of claim 18 wherein the effective amount comprises an amount sufficient to treat Malaria.

20. A composition according to claim 8, for use in the treatment of Malaria, which further comprises an anti-Malaria effective amount of a pyrimidine nucleotide precursor selected from uridine and cytidine.

21. A method of treating Malaria comprising administering an anti-malaria effective amount of a compound as in claim 1, to a patient with Malaria.

22. A composition according to claim 18, for use in the treatment of cancer, which further comprises an effective amount of a blocking agent selected from dipyridamole, dilazep and nitrobenzyl thioinosine.

* * * * *